United States Patent [19]

Dreher

[11] 4,351,679
[45] Sep. 28, 1982

[54] LABEL-LEAFLET APPLYING APPARATUS

[75] Inventor: Hans C. Dreher, Dallas, Pa.

[73] Assignee: Culbro Corporation, New York, N.Y.

[21] Appl. No.: 176,590

[22] Filed: Aug. 8, 1980

[51] Int. Cl.³ .............................................. B65C 9/08
[52] U.S. Cl. ...................... 156/70; 53/590;
 156/350; 156/352; 156/383; 156/521; 156/567
[58] Field of Search ............... 156/518, 517, 520, 521,
 156/522, 566–568, 352, 350, 70, 383; 198/377;
 53/590

[56] References Cited

U.S. PATENT DOCUMENTS

| Re. 23,512 | 6/1952 | Von Hofe | 156/320 |
|---|---|---|---|
| 1,583,411 | 5/1926 | Meyer | 156/559 |
| 1,686,354 | 10/1928 | Wallace | 40/310 |
| 1,850,369 | 3/1932 | Andrews | 40/310 |
| 1,871,677 | 8/1932 | Ernold | 156/476 |
| 1,873,967 | 8/1932 | Klute | 156/559 |
| 2,166,497 | 7/1939 | Kroedler et al. | 156/559 |
| 2,584,632 | 2/1952 | Southwick | 156/289 |
| 2,614,349 | 10/1952 | Barnes | 40/2 |
| 2,725,101 | 11/1955 | Van Hofe | 83/251 |
| 2,946,281 | 7/1960 | Sohn | 10/227 |
| 2,956,612 | 10/1960 | Gaines et al. | 156/355 |
| 3,035,380 | 5/1962 | Leavens | 53/47 |
| 3,038,391 | 6/1962 | Von Hofe et al. | 493/6 |
| 3,084,621 | 4/1963 | Guastavino | 101/181 |
| 3,107,566 | 10/1963 | Archer | 83/33 |
| 3,138,508 | 6/1964 | Fairest | 156/215 |
| 3,140,214 | 7/1964 | Von Hofe | 156/354 |
| 3,151,014 | 9/1964 | Jackson | 156/521 X |
| 3,193,430 | 6/1965 | Messmer et al. | 156/355 |
| 3,253,544 | 5/1966 | Von Hofe | 101/426 |
| 3,478,870 | 11/1969 | Segel | 206/46 |
| 3,485,697 | 11/1969 | Reed | 156/265 |
| 3,488,241 | 1/1970 | Faltot | 156/351 |
| 3,506,524 | 4/1970 | Von Hofe | 156/517 |
| 3,522,134 | 7/1970 | Von Hofe | 156/571 |
| 3,531,354 | 9/1970 | Hefzinger | 156/383 |
| 3,532,503 | 10/1970 | Thiele | 156/521 |
| 3,536,550 | 10/1970 | Von Hofe | 156/64 |
| 3,553,041 | 1/1971 | Von Hofe | 156/378 |
| 3,553,049 | 1/1971 | Wolff | 156/250 |
| 3,594,257 | 5/1971 | Von Hofe | 156/455 |
| 3,607,537 | 9/1971 | Von Hofe | 156/277 |
| 3,630,805 | 12/1971 | Iried | 156/354 |
| 3,697,300 | 7/1970 | Von Hofe | 428/136 |
| 3,756,899 | 9/1973 | Von Hofe | 156/510 X |
| 3,776,798 | 12/1973 | Milano | 156/269 |
| 3,779,829 | 12/1973 | Wolff | 156/361 |
| 3,823,050 | 7/1974 | La Merg | 156/493 |
| 3,850,083 | 11/1974 | Falcon | 156/257 X |
| 3,856,607 | 12/1974 | Faltot | 156/360 X |
| 3,864,187 | 2/1975 | Carter | 156/364 |
| 3,871,943 | 3/1975 | Zodrow | 156/521 |
| 3,897,945 | 8/1975 | Faltot et al. | 271/227 |
| 3,954,542 | 5/1976 | Solomon | 156/567 X |
| 3,955,502 | 5/1976 | Von Hofe | 101/426 |
| 3,955,503 | 5/1976 | Von Hofe | 101/426 |
| 3,985,605 | 10/1976 | Treiber | 156/384 |
| 4,009,070 | 2/1977 | Linmans | 156/559 |
| 4,025,382 | 5/1977 | Del Rosso | 156/497 |
| 4,029,537 | 6/1977 | Kish | 156/497 |
| 4,218,863 | 8/1980 | Howard | 198/377 X |
| 4,233,331 | 11/1980 | Lemke et al. | 156/521 X |

Primary Examiner—David A. Simmons
Attorney, Agent, or Firm—Morgan, Finnegan, Pine, Foley & Lee

[57] ABSTRACT

An apparatus for applying labels and/or leaflets to containers in a continuous single run operation includes a product entry station, a conveyor for transporting the containers in a horizontal position through the apparatus, applicators for applying in succession leaflets and labels to the underside and upper surface, respectively of the containers, and a product discharge station where properly processed containers are exited for further processing and improperly processed containers are rejected.

31 Claims, 7 Drawing Figures

LABEL-LEAFLET APPLYING APPARATUS

BACKGROUND OF THE INVENTION

1. Field of the Invention

The present invention relates to an apparatus for applying articles to containers, and more particularly to a high speed apparatus adapted to apply labels and/or leaflets to containers such as pharmaceutical bottles in a continuous through-put manner.

2. The Prior Art

Several types of apparatus for applying labels to containers, bottles and the like are known and in common use. One type of apparatus employs labels that are cut, stacked in a hopper and fed to a label applicator mechanism that holds each label for a period of time and then applies the label to a container which is fed to the applicator. Typically, the containers are fed to the applicator in an upright position and the entire label cutting and label and container feeding procedure is effected in an intermittent motion or stop-start manner to insure the accurate application of the labels. Unfortunately, such apparatus suffer from several shortcomings such as the curling and sticking of cut labels, variable label size and problems associated with the verification of many loose individual labels. The verification problems are especially troublesome in the pharmaceutical packaging industry. Another shortcoming with the described apparatus is that its stop-start mode of operation is time wasteful and thus not as efficient or desirable.

Another type of known labelling apparatus employs rolls of web material from which individual labels are cut and then fed and applied to containers. Known apparatus of this type, however, also suffer from the shortcoming of operating in the inefficient stop-start mode with the articles to be labelled being fed to the label applicator in the upright position. In addition, known apparatus of this type which are used in the pharmaceutical packing industry, typically include label verification mechanisms that inefficiently shut down the apparatus upon detection of a single unverified label, even though that label might be atypical of the rest of the roll. For example, it is known to use punched holes for label verification marks, and with such a system, it is not uncommon for the verification holes to be incompletely punched. In such a situation, known verifying means, which verify each individual label, would detect the incompletely punched label as an unverified label and generate a signal effecting machine shut down, even though the particular label detected as unverified, and the remaining roll of labels, are in fact correct.

As indicated above, in addition to a labelling apparatus, the present invention relates to an apparatus that is adapted to apply leaflets, as well as labels, to containers. Such provision is particularly applicable in the sales of pharmaceuticals, where governing United States Food and Drug Administration regulations require that a leaflet, known as a package insert or outsert, which contains information such as dosages, administration, precautions, etc., be distributed with each pharmaceutical product sold to pharmacists. Some pharmaceutical companies attempt to satisfy this requirement by merely including a group of loose leaflets within the carton of products sold. This is undesirable, however, because pharmaceutical companies typically sell their products through wholesalers and distributors, who in turn must then sort the loose leaflets to make sure that the correct leaflet is provided with its corresponding product container when it is sold to a pharmacist. Other pharmaceutical companies package each product container in an individual carton and insert a loose leaflet in each carton. This, too, is undesirable, in that it increases the cost of packaging, and because pharmacists are likely to store the product sans carton (and leaflet) for space-saving reasons.

Some pharmaceutical companies attempt to avoid these problems by gluing each leaflet to its corresponding product container. Other companies attach the leaflets to containers by means of a shrinkable plastic film member which encloses the product container and leaflet. In both types of affixation, however, the leaflet is loose and subject to loss once it has been removed from the container.

It is clear that it would be very desirable to have, and it is the broad object of the present invention to provide, a high speed apparatus that is adapted to apply labels and/or leaflets to containers in a continuous through-put single run operation. The specific objects of the present invention are as follows:

To provide a high speed apparatus for applying labels to containers in a continuous through-put operation;

to provide a high speed apparatus for folding leaflets and applying the leaflets to containers in a continuous through-put operation, the leaflets being applied so that they may be readily re-affixed to the container after having been removed therefrom;

to provide a high speed apparatus for folding leaflets and applying the leaflets, as well as labels to containers in a continuous, through-put single pass operation whereby the labels and leaflets are applied to opposite faces of the containers;

to provide a high speed apparatus for applying labels and/or leaflets to containers in a continuous single run operation, the apparatus having verification means for shutting down the machine only after it is determined that the machine has not been loaded with the correct labels, while still assuring that only correctly labeled containers are released for distribution.

SUMMARY OF THE INVENTION

In accordance with the above-recited objectives, the present invention provides an apparatus for applying labels and/or leaflets to containers in a continuous single operation. In broadest terms, the subject apparatus includes a product entry station, an application station, a product exit or discharge station, container conveyor means for transporting containers in a horizontal position through the apparatus, and container reorientation means for placing processed container in the upright position for future processing. Preferably, the apparatus also includes a leaflet folder, means for conveying folded leaflets to a point of application; means for mating a strip of thermoplastic tab material with each leaflet and adhesively activating the end portions of each tab; and means for applying in succession a leaflet-tab combination to one face of each container and then a label to the other face of the container, the leaflets being reattachably secured to the containers by the tabs. In addition, the subject apparatus also preferably includes label verification means which effects machine shut down only after it has been determined that, in all probability, an entire roll of label web material is improper.

DETAILED DESCRIPTION OF THE PREFERRED EMBODIMENT

Figure 1:
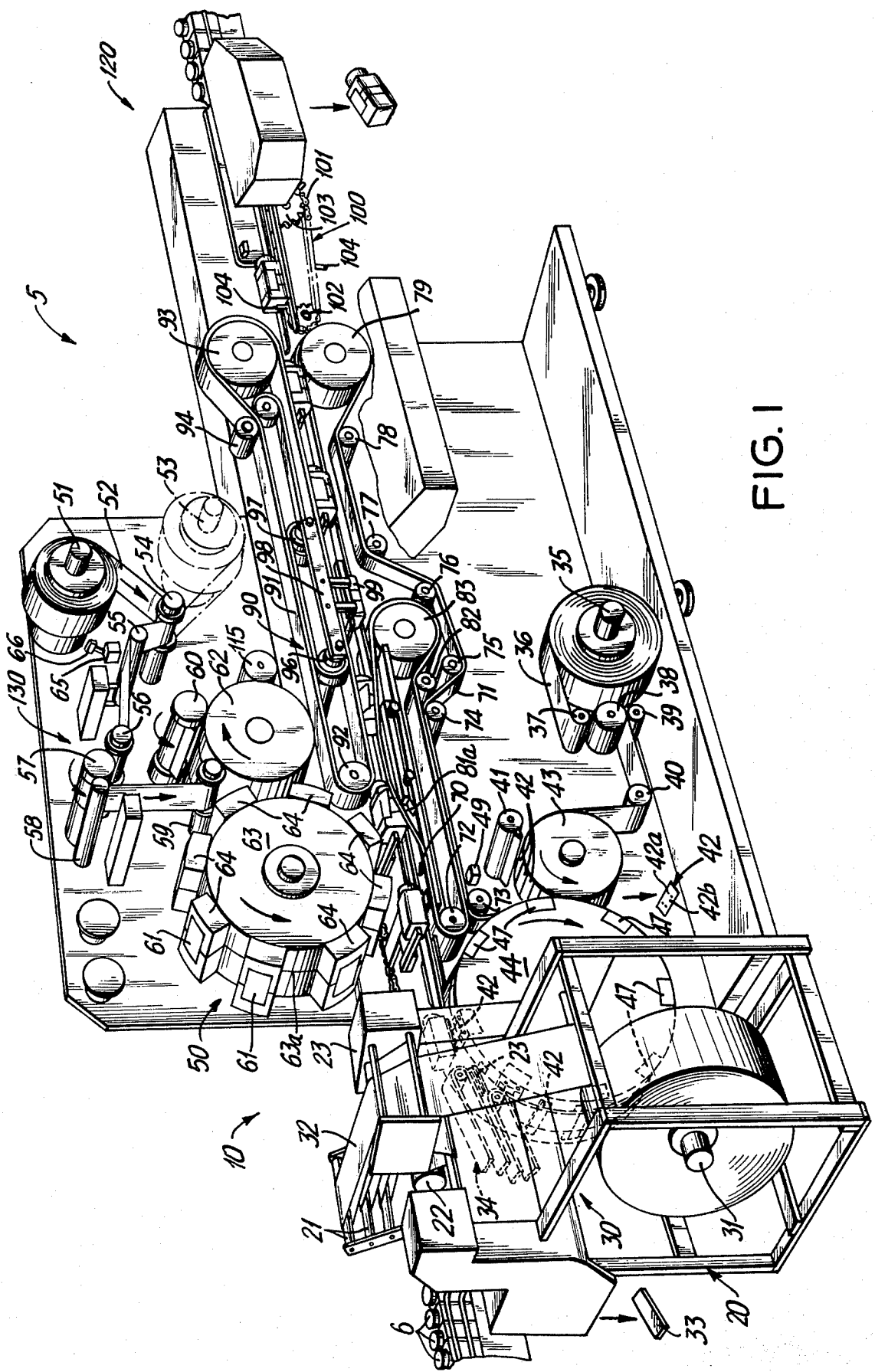
FIG. 1 is a perspective schematic diagram, phantom in part, of the overall label-leaflet applying apparatus of the present invention.

Referring to FIG. 1, there is illustrated a perspective view schematic diagram of the overall apparatus of the present invention. The apparatus, which is designated generally by reference number 5, includes in broadest terms, a product entry station 10, a label application station 50, and a product exit station 120. As illustrated, the subject apparatus 5 also includes a label verification and registration station 130 which is part of the overall label application station 50 and in addition a leaflet application station 30, for use in conjunction with particular applications where it is desirable to attach a leaflet as well as apply a label to a container. One such application would be in the pharmaceutical industry where a package insert must be included with certain pharmaceutical product containers.

Figure 2:
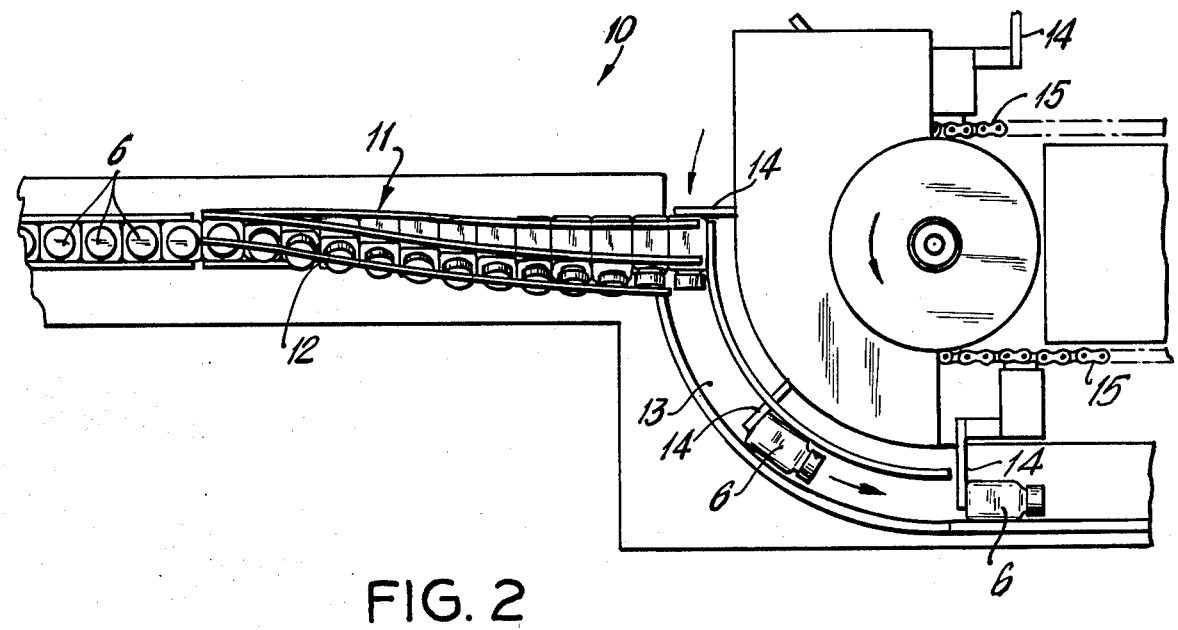
FIG. 2 is a plan view schematic diagram of the entry station of the apparatus of the present invention.

Turning now to FIGS. 1 and 2, the product entry station 10 of the subject apparatus includes conveyor means 11 for receiving the containers 6 to which labels and/or leaflets are to be applied and for transporting the containers towards the actual label and leaflet applying mechanisms of the apparatus. As shown in the Figures, the containers 6 are received on conveyor 11 in the upright position, typically from an on-line container filler and capper (not shown). In accordance with the continuous through-put operation of the subject apparatus, product entry station 10 also includes means for orientating containers 6 in horizontal position such that a label and leaflet may be applied successively to opposite sides of each container in a continuous, non-stop manner. Referring to FIG. 2, the orientation means may comprise a curved rail member 12 which gradually rotates each container 6 to the horizontal position as each container 6 is moved along conveyor 11 to an entry channel 13. At the mouth of entry channel 13 a finger member 14 engages each container 6 for guiding each container through entry channel 13 in a predetermined spaced apart relationship with adjacent containers. Typically, finger members 14 may be operated by means of an endless chain member 15 driven by a motor driver (not shown).

Figure 3:
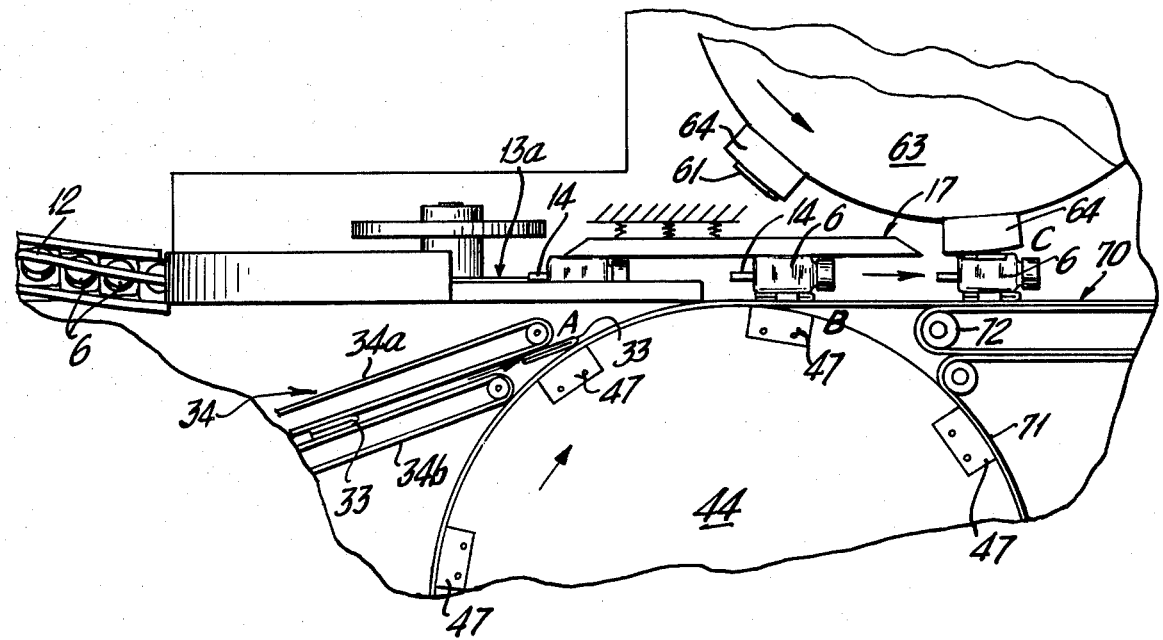
FIG. 3 is an elevational view schematic diagram of the leaflet and label applying mechanisms of the apparatus of the present invention.

Referring now to FIGS. 1 and 3, the leaflet application station 30 of the subject apparatus includes means 34 for conveying folded leaflets 33 in a particularly spaced relationship towards a leaflet applicator 44 to be described below. As shown most clearly in FIG. 3, conveyor 34 may comprise a pair of superimposed endless belt members 34a and 34b. It will be noted that while the subject apparatus may be adapted simply to receive folded leaflets and convey them to the leaflet applicator, it is preferable for the sake of simplicity and efficiency that the subject apparatus include a leaflet folder 20 for cutting leaflets from a web of stock material and folding them to the desired size. Thus, as shown in FIG. 1, the leaflet folder 20 adapted to be used with the subject apparatus typically includes means 31 for supporting a roll of printed web stock material 32 from which the individual leaflets 33 are to be formed. Leaflet folder 20 also includes a plurality of web separator rollers 21, a cutter 22, and a registration member 23 for accurately aligning the portions of the leaflet web to be cut. Because some package inserts are printed on other than full width stock such as half width stock or other it is preferable that folder 20 be adapted to fold a wide range of widths of stock such that the overall folded leaflet 33 has the same size despite differences in original stock width. Leaflet folder 20 further includes a timed feed mechanism (not shown) for depositing each folded leaflet on conveyor 34 such that each folded leaflet is spaced apart from the next leaflet a predetermined distance.

In accordance with the present invention, each folded leaflet 33 is attached to one side (the underside) of a product container 6 by means of a thermoplastic tab member 42. Thus, referring to FIG. 1 the leaflet application station 30 of the subject apparatus further includes a roll member 35 for supporting a roll of thermoplastic web material 36. The web material is fed by means of drive roller 38 and idler rollers 37, 39, and 40 to a tab cutter drum 43. A tab cutter 41, disposed over cutter drum 43, cuts individual tabs 42 from the web 36 on four equally spaced positions on drum 43. Drum 43 includes vacuum means for selectively retaining the cut tabs 42 on its surface. Disposed adjacent to tab cutter drum 43 is tab applicator drum 44 which, in accordance with the described embodiment, includes eight equally spaced head members 47 for holding tabs 42 in a predetermined spaced relationship. Head members 47 include vacuum means for selectively retaining tabs 42 on its surface. In addition, head members 47 include means for heating, and thus adhesively activating, only the end portions 42a of each tab member.

Referring still to FIGS. 1 and 3, tab applicator drum 44 is rotated at a pre-determined speed by control means (not shown) such that each spaced tab member 42 held thereon meets one of the folded leaflets 33 travelling along conveyor 34 (folded edge leading) at point A of FIG. 3 and further such that a leaflet-tab combination meets a container 6 at application point B of FIG. 3, containers 6 being transported by fingers 14 at the same speed as leaflets 33 along conveyor 34 and tabs along drum 44. It will be noted that tab cutter drum 43 rotates twice for every revolution of applicator drum 44. However, because cutter drum 43 has a diameter one half that of applicator drum 44 the peripheral velocities of both drums are equal.

Referring specifically to FIG. 3, it will be noted that as each container 6 reaches the exit portion 13a of entry channel 13 it is engaged by a stabilizer member 17. As a folded leaflet 33 reaches point A of applicator drum 44 it is positioned onto a corresponding tab member 42 and is retained against the surface of a head 47 (see FIG. 1)

by the vacuum means thereof. As drum 44 continues to rotate, the tab-leaflet combination comes into contact with a container at point B. Stabilizer member 17, may be spring biased and upwardly and downwardly adjustable.

It will be noted that an endless belt member 71, which is part of an overall conveyor means 70 which will be described in more detail below, is partially disposed around tab applicator drum 44 in a central groove (not shown) in drum 44. Thus, the surface of belt 71 is flush with the surface of drum 44. In operation, tabs 42, which are received from tab cutter drum 43, overlap belt 71 and the surface of drum 44, belt 71 and drum 44 being driven at the same speed. Each leaflet 33 is then positioned onto a tab 42 at position A. Each tab-leaflet combination then meets a bottle 6 at position B at which point belt 71 disengages from drum 44 and carries the tab-leaflet-bottle combination with it to label application station 50 and further through the apparatus. The downward action of stabilizer 17 on each bottle 6 along with the fact that belt 71, drum 44, and finger members 14 are driven in timed relation to one another insure that each tab-leaflet bottle combination is neatly and precisely formed and maintained in the proper orientation for further processing.

Figure 4:
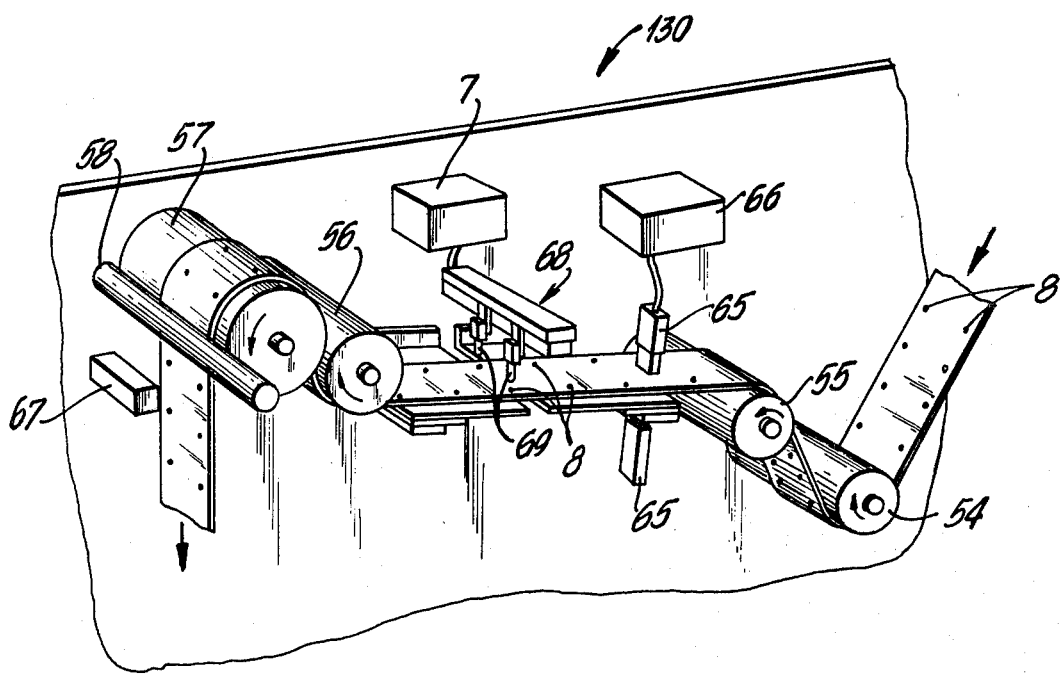
FIG. 4 is a partial perspective view schematic diagram of the label web verification and registration station of the apparatus of the present invention.

Turning now to FIGS. 1, 3 and 4, the label application station 50 of the subject apparatus is illustrated. More particularly, label application station 50 includes a roll member 51 for supporting a roll of web material 52 upon which labels for the particular container to be labeled are printed. Preferably, web material 52 is a thermoplastic web material. In addition, in order to keep down time to a minimum, it is preferable that a spare label roll member 53 be included as a back up to roll 51. Label web 52 is conveyed via guide rolls 54, 55, 56, 57, 58 and 59 to a label cutter drum 62. A label cutter 60, disposed over label cutter drum 62, cuts individual labels 61 from the label web 52 on label cutter drum 62. Label drum 62 includes vacuum means for selectively retaining the individual cut labels 61 on its surface. In addition, drum 62 rotates at a speed greater than that of the web feed such that it (drum 62) advances the cut labels 61 so that the labels are spaced a predetermined distance from one another. Adjacent label cutter drum 62 is a label applicator drum 63 having a plurality of particularly spaced apart applicator head members 64. Each applicator head member 64 includes vacuum means for selectively retaining an individual cut label 61, and also heating means for activating the thermoplastic control means (not shown) causes label applicator drum 63 to rotate at a predetermined speed such that a label bearing applicator member 64 meets a container-leaflet-tab combination at point C of the apparatus whereupon the vacuum in the particular applicator head member 64 is terminated so as to release the label, which having been heat activated, adheres to the upper surface of the container 6. The label and leaflet bearing container then moves along belt 71 of conveyor means 70 to the label and tab securing mechanisms of the subject apparatus.

Referring to FIG. 1, it will be noted that label applicator drum 63 may be adapted to be spread apart along seam 63a and an insulator positioned in the space thus formed such that only selected portions of the labels 61 will be adhesively activated.

Figure 5:
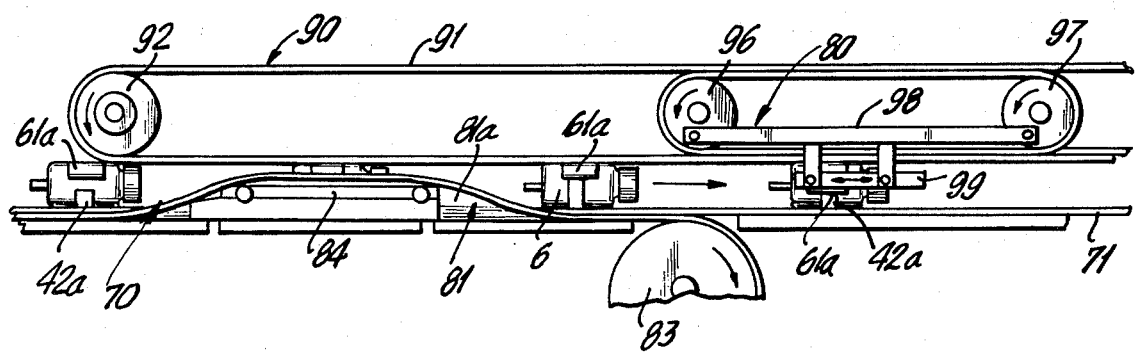
FIG. 5 is a partial elevational view schematic diagram of the leaflet and label securing mechanisms of the apparatus of the present invention.
Figure 6:
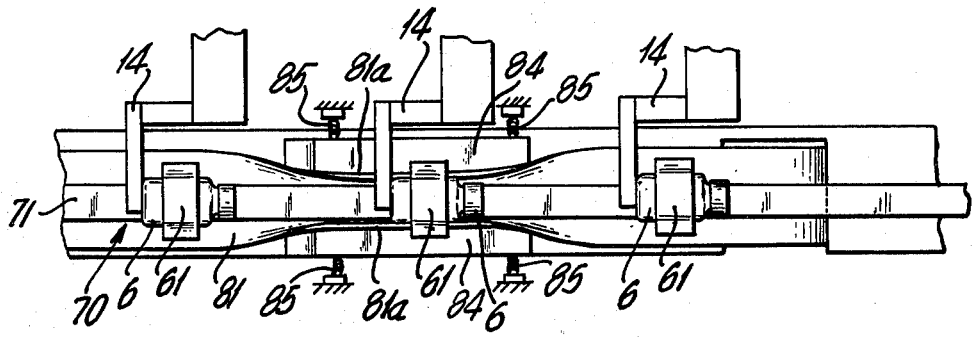
FIG. 6 is a partial plan view schematic diagram of the leaflet securing mechanism of the apparatus of the present invention.

Referring now to FIGS. 1, 5 and 6, immediately after a label is applied to a container 6 at application point C, the label-container-leaflet-tab combination is fed by conveyor means 70 to a downstream stabilizer means 90 which, as illustrated, may comprise an endless belt member 91 driven by rollers 92, 93 and 94. In operation, stabilizer belt 91 is driven at the same speed as conveyor means 70 such that equal forces are placed on the top and bottom surface of each container 6 thus maintaining a stable container orientation as each container is engaged by the tab and label securing mechanisms of the apparatus to be described below.

Referring specifically to FIGS. 5 and 6, it will be noted that conveyor means 70 may actually comprise a pair of partially overlapping endless belt members, namely, a tab wiper belt member 81 which is driven by rollers 72, 82 and 83, and a narrower support belt member 71 which is partially disposed on wiper belt 81 and drum 44 and which is driven by drum 44 and roller 79 via guide rollers 72–78 at the same speed a wiper belt 81. Opposed lateral portions 81a of wiper belt 81 are maintained in an upward position by a pair of opposed lateral support members 84 which are spring biased by spring members 85 for flexibility. As a label-container-leaflet-tab combination is conveyed toward belt portions 81a, said lateral belt portions 81a gradually wipe the heat activated end portions 42a of each tab against the side of the container 6 for securing the tab and the leaflet to the container. It will be noted that only end portions 42a of each tab have been heat activated by drum member 44 such that the tab central portion 42b thereof remains spaced apart from and in slidable engagement with its associated leaflet. Thus, the leaflet may be easily reattached after removal. In addition, it will be noted that because wiper belt 81 and support belt 71 are driven at the same speed, the tab ends 42a are accurately and neatly secured to the container sides.

Still referring to FIGS. 1 and 5, a label securing mechanism 80 is disposed downstream of leaflet wipers 81a. As illustrated, label wiper mechanism 80 may comprise an endless belt member 95 which connects rollers 96 and 97 in timed relationship. A linkage bar member 98 connects rollers 96 and 97 along their opposed faces such that the parallel pair of linkage members 98 straddle support conveyor belt 71. Linkage bar members 98 are rotatably mounted on rollers 96 and 97 such that bar members 98 rotate along with said rollers. A horizontal wiper member 99 extends from each linkage bar member 98, each wiper being adapted to rotate along with its associated linkage bar.

Thus, as a container 6 passes under rollers 96 and 97 wiper members 99 engage the extended end portions 61a of the label and effect, by their rotational movement, the wiping of the label end portions 61a against the sides of the container for securing the label 61 thereto. Preferably, secured label end portions 61a overlap the ends 42a of the leaflet holding tab member 42 thus serving as an additional tab securing means. This overlap is easily effected because of the successive applications and securing of the subject labels and tabs.

Figure 7:
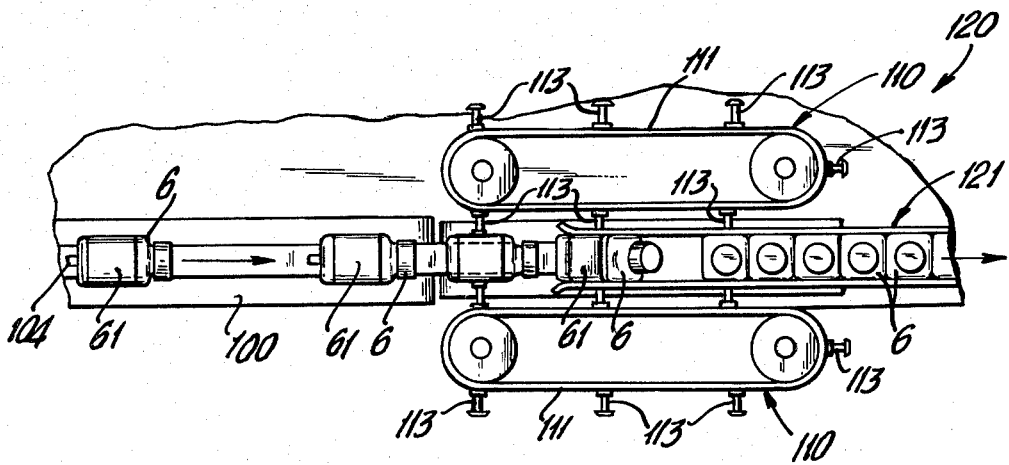
FIG. 7 is a partial plan view schematic diagram of the container reorientation mechanism and exit station of the apparatus of the present invention.

Referring to FIGS. 1 and 7 a conveyor means 100 is disposed downstream of the leaflet and label securing mechanisms and adjacent the nip of rollers 93 and 79 for receiving the leaflet-label bearing containers and conveying them towards the apparatus exit station 120. As illustrated (FIG. 1) conveyor means 100 may comprise an endless chain member 101 driven by sprockets 102 and 103. Chain member 101 includes a plurality of particularly spaced apart lugs 104 which engage the rear portions of each container 6 for further conveying of the containers through the apparatus.

Turning now specifically to FIG. 7, the apparatus exit station 120 includes a product reorientation member 110 which re-orients the leaflet and label bearing containers 6 from the horizontal position to the upright position and deposits them on a discharge conveyor 121 which conveys the containers out of the apparatus for further processing such as bulk packaging. As illustrated, reorientation member 110 may comprise a pair of opposed endless chain members 111, each of which having a plurality of rotatable and reciprocable spaced gripping members 113. As each horizontal container reaches the downstream end of conveyor 100 a pair of associated gripping members 113, one from each of chain members 111, comes together against the sides of a container 6 so as to take hold of the container. As gripping members 113 move downstream, they rotate so as to gradually re-orient the container 6 from the horizontal position to the vertical position. As each associated pair of gripping members 113 reaches the downstream end of re-orientation means 110, the individual gripping members separate so as to deposit the container 6 in an upright position on discharge conveyor 121.

As indicated above, the subject apparatus is particularly adapted for use in the pharmaceutical industry. With regard to this particular application, it will be appreciated that the subject apparatus should preferably include means for verifying that the correct label is applied to a particular product container and that only the desired end product, i.e., a container to which the correct label and/or leaflet has been applied is discharged at exit station 120 of the apparatus. Accordingly, reference is now made to FIGS. 1 and 4 wherein the verification station of the subject apparatus, which is designated generally by reference numeral 130 is shown as being in substantial part associated with the label application station 50 described above.

In accordance with the preferred embodiment of the present invention, the subject apparatus is adapted to use label web material 52 containing preprinted label indicia. In addition, as shown in FIG. 4, label web 52 includes particularly arranged verification and registration marks 8, each pair of marks being associated with a single label. As illustrated, marks 8 may take the form of punched holes. Before discussing label verification specifically it will be noted that it is common in the labelling industry to splice together portions of partial rolls of label web material. Thus, the subject apparatus includes a splice detector 65 which is disposed downstream of feed rollers 54 and 55 for detecting every instance where a splice exists. In addition, the subject apparatus includes memory means 66, which is responsive to the output of detector 65, for tracking the splice containing label and the product container to which it is applied. A splice rejector (not shown) is responsive to the output of memory means 66 and is associated with gripper members 113 to effect the withdrawal of grippers 113 from a container to which a spliced label has been applied and thus effects the discharge of such container.

Turning now to the label verification means per se, the subject apparatus includes a label verifier 68 which is disposed downstream to feed rollers 54 and 55. As illustrated, label verifier 68 includes a pair of spaced apart scanners 69 for determining whether the label web verification and registration marks 8 are correct for the particular label to be applied. Scanners 69 are movable relative to one another such that they may be locked into a spacing that is precisely aligned with the actual spacing of the verification marks 8 on a correct label web. In addition, label verifier 68 includes a timing mechanism (not shown) which activates scanners 69 at the precise moment a pair of verification marks 8 is supposed to pass thereunder.

In accordance with the present invention, while it is important that incorrectly labeled containers not be mixed with correctly labeled containers at the exit station of the apparatus, it is undesirable to shut down the entire operation of the apparatus immediately after a single unverified label is detected. For example, where label marks 8, take the form of punched holes, it is not uncommon for one or the other of the holes to be incompletely punched, and although a label web may be actually correct, scanners 69 would detect an unverified label. In such situations, it is preferable that machine shut down not be effected after the detection of a single unverified label, but rather only after it has been determined that in all likelihood the entire label web is improper.

Accordingly, the subject apparatus includes a counter member 7 which is responsive to the output of scanners 69 for counting the number of consecutive unverified labels detected by scanners 69. Counter 7 may be set to a predetermined number to which the user believes indicates that in all probability the entire roll of label web material is improper. Having counted to said predetermined number, counter 7 generates a signal effecting the shutting down of the machine to prevent the continued application of incorrect labels to containers. Because the subject apparatus is adapted to be used with pre-printed label webs, for all practical purposes there will never be isolated improper labels on a web but only an entire string of improper labels. Thus, there is no need to verify each individual label on a label web, but rather only the label as a whole.

After machine shut down any unverified labels, and/or containers to which unverified labels have been applied may be manually removed from the apparatus before restarting. For extra safety, the apparatus could be designed such that even when less than the predetermined number of consecutive unverified labels has been detected by counter 7 each unverified label is traced such that the product container to which it is applied is rejected at the product exit station by the dropping of the improperly labeled containers by the pertinent gripping members 113 at reorientation means 110. In addition, it may be desirable to include means for defacing an unverified label after it has been applied to a container such that it is easily distinguishable from correctly labeled containers.

Still referring to FIG. 4, after being scanned by label verification unit 68, the label web is conveyed by feed rollers 56 and 57 past a registration scanner 67 which detects the location of the verification/registration marks 8 for the purpose of electronically communicating with label cutter 60 (see FIG. 1) the correct portion of the web to be cut to form full individual labels. Registration scanner 67 "knows" where the marks should be located, and it scans for the actual location of the marks. If there is a discrepancy, the registration scanner communicates this to a feed control mechanism (not shown) which either accelerates or slows the label web feed speed.

Turning again specifically to FIG. 1, the subject apparatus also includes a tab scanner 49 which communicates electronically with rejector means associated with the label cutter drum 62 and leaflet folder 20 respectively. For example, scraper means 115 disposed adjacent label cutter drum 62 may be included to selectively scrape a label off of drum 62. Thus, when scanner 49 detects that there is no tab in an appropriate location on the tab cutter drum 43 it communicates a signal to the scraper means 115 effecting the discarding (scraping off) of the corresponding label that would otherwise be applied to a container. A component missing sensor, disposed at exit station 120 detects whether a label, leaflet or tab is not applied to a container, and in such an instance generates a signal effecting the discarding of such faulty container by the separation of the pertinent pair of gripping members 113 of re-orientation means 110.

It will be noted that while the subject apparatus has been described as being adapted to apply a single folded leaflet to each container, it is also adapted to apply a packet of leaflets to a container if desired. In such situations the above described label and leaflet applying and securing operations of the apparatus will be the same. However, instead of having an on-line folder 20 as part of the apparatus it is preferable to have a separate apparatus that folds the individual leaflets and then arranges them in packets, for example, by applying a widthwise and lengthwise tab around the folded leaflets. The packet may then be fed into a hopper for deposit onto leaflet conveyor 34.

While the preferred embodiment of the subject invention has been described and illustrated, it would be obvious that various changes and modifications can be made therein without departing from the spirit of the invention which should be limited only by the scope of the appended claims.

What is claimed is:

1. A high speed apparatus for applying labels to containers in a continuous through put operation, the apparatus having container entry and exit stations and a label applicator station, comprising:
   conveyor means for transporting said containers through the apparatus from said entry station to said exit station at a constant predetermined speed and in a predetermined spaced relationship with one another;
   means for feeding a continuous label web to said label application station, said label web having label indicia and particularly oriented verification marks disposed therein for each individual label;
   means disposed upstream of said label application station for cutting each individual label from the label web;
   means for conveying said cut individual labels to said application station;
   label applicator means disposed at said label application station for receiving a cut label and applying said label to a container while the container is in motion as it passes said label application station;
   control means for selectively operating said label applicator means at the precise time one of said spaced apart containers passes said label applicator means;
   label verification means disposed upstream of said label application station including splice sensing means for detecting portions of the label web which have been spliced together;
   tracking means responsive to said splice sensing means for tracking the spliced label web portion and the container to which it is applied; and
   means responsive to said tracking means for segregating said container to which a spliced label web portion has been applied from properly labeled containers.

2. An apparatus as in claim 1 which further includes orientation means, disposed at said entry station, for receiving each of said containers in a vertical position and placing each of said containers in a horizontal position for conveyance through the apparatus.

3. An apparatus as recited in claim 2 wherein said orientation means comprises a curved rail member for receiving said container in a vertical position and rotating said container to a horizontal position.

4. An apparatus as in claim 1 which further includes re-orientation means, disposed adjacent said exit station, for receiving each of said containers in a horizontal position and placing each of said containers in the vertical position for discharge from the apparatus exit station.

5. An apparatus as in claim 4 wherein said reorientation means comprises a plurality of spaced apart rotatable gripper members disposed on either side of said conveyor means; means for bringing together an opposed pair of said gripper members for gripping each of said containers; means for rotating said gripper members to effect the rotation of each container from the horizontal position to the vertical position; and means for withdrawing said opposed pair of gripper members to effect the release of each container after it has been reoriented.

6. An apparatus as in claim 1 wherein said verification means further includes:
   verifier means for detecting the absence of said particularly oriented verification marks disposed on said label web as indicative of an unverified label;
   counter means responsive to said verifier means for recording up to a predetermined number the number of consecutive label web portions for which said particularly oriented verification marks are absent; and
   means responsive to said counter means for terminating the operation of the apparatus only if said counter means has counted up to the said predetermined number.

7. An apparatus as in claim 6 which further comprises memory means responsive to said verifier means for tracking each unverified portion of the label web for which the absence of said particularly oriented verification marks has been detected as well as the container to which such unverified label web portion has been applied; and rejector means responsive to said memory means disposed at said exit station for rejecting each of said unverified label bearing containers.

8. An apparatus as in claim 1 which further includes label securing means for wiping the ends of each label against the sides of the container to which said label is applied so as to secure said label to each container.

9. An apparatus as in claim 1 which further comprises:
   container stabilizer means for maintaining the orientation of the containers after label application and while the labels are being secured to the containers by said label securing means, said stabilizer means comprising an endless belt member that engages the top surface of each container and exerts a downward force thereon during the operation of said label securing means.

10. An apparatus for use in an automatic labeling machine to verify a continuous label web having particularly oriented verification marks for each individual label comprising:
- detector means for detecting the absence of said particularly oriented verification marks disposed on said label web as indicative of an unverified label;
- counter means responsive to said detector means for recording up to a predetermined number the number of consecutive label web portions for which said particularly oriented verification marks are absent; and
- means responsive to said counter means for terminating the operation of the labeling machine when said counter means has counted up to said predetermined number.

11. An apparatus for controlling the output of a container labeling machine that employs a continuous label web from which individual labels are cut and applied to containers comprising:
- splice sensing means for detecting portions of the label web which have been spliced together;
- control means responsive to said splice sensing means for tracking each spliced label web portion and the container to which it is applied; and
- rejector means responsive to said tracking control means for segregating said container to which a spliced label has been applied from properly labeled containers.

12. A high speed apparatus for applying leaflets to containers in a continuous through put operation, the apparatus having container entry and exit stations and a leaflet application station, comprising:
- conveyor means for transporting said containers through the apparatus from said entry station to said exit station at a constant predetermined speed and in a predetermined spaced relationship with one another;
- means adjacent said leaflet application station for storing a plurality of leaflets;
- means adjacent said leaflet application station for storing a plurality of adhesively activatable tab members;
- means for supporting a roll of continuous leaflet web material;
- cutting means for severing individual leaflets from the leaflet web;
- folding means for folding each individual leaflet to a form suitable for attaching to a container;
- discharge means for placing each folded leaflet in said leaflet storing means;
- leaflet applicator means disposed at said leaflet application station for receiving a tab member and a leaflet, such that the leaflet is superimposed over the center portion of said tab to form a tab/leaflet combination, and applying a tab/leaflet combination to a container said leaflet applicator means including means for adhesively activating only the end portions of each tab;
- means for conveying a leaflet and a tab to said leaflet application; and
- control means for mating each leaflet with a tab, and each tab/leaflet combination with a container.

13. An apparatus as in claim 12 which further includes orientation means, disposed at said entry station, for receiving each of said containers in a vertical position and placing each of said containers in a horizontal position for conveyance through the apparatus.

14. An apparatus as recited in claim 13 wherein said orientation means comprises a curved rail member for receiving said container in a vertical position and rotating said container to a horizontal position.

15. An apparatus as in claim 12 which further includes reorientation means, disposed adjacent said exit station, for receiving such of said containers in a horizontal position and placing each of said containers in the vertical position for discharge from the apparatus exit station.

16. An apparatus as in claim 15 wherein said reorientation means comprises a plurality of spaced apart rotatable gripper members disposed on either side of said conveyor means; means for bringing together an opposed pair of said gripper members for gripping each of said containers; means for rotating said gripper members to effect the rotation of each container from the horizontal position to the vertical position; and means for withdrawing said opposed pair of gripper members to effect the release of each container after it has been reoriented.

17. An apparatus as in claim 12 which further includes tab securing means disposed downstream of said tab applicator means, said tab securing means comprising an endless belt member on which the containers are carried, said tab securing means further including a pair of lateral support members for maintaining in an upstanding position opposed lateral portions of said endless belt member such that as a container-leaflet-tab combination engages the upstanding portions of said endless belt, said upstanding portions effect the wiping up of the activated end portions of each tab against the side portions of its associated container thus releasably securing the leaflet to its respective container.

18. An apparatus as in claim 13 which further includes container stabilizer means disposed opposite said leaflet applicator means for exerting a force against each container substantially opposite to that exerted by said leaflet applicator means as each tab/leaflet combination is applied to a container.

19. An apparatus as in claim 12 which further comprises:
- detector means disposed adjacent said container exit station for detecting the absence of a tab/leaflet combination; and
- means responsive to said detector means for discarding any container which does not have a tab/leaflet combination.

20. A high speed apparatus for applying labels and leaflets to containers in a continuous through put operation, the apparatus having container entry and exit stations, a leaflet applicator station and a label applicator station, comprising:
- conveyor means for transporting said containers through the apparatus from said entry station to said exit station at a constant predetermined speed and in a predetermined spaced relationship with one another, said conveyor means including means for maintaining said containers in a horizontal orientation while passing through said label application station and while said labels are applied;
- means adjacent said label application station for storing a plurality of adhesively activatable labels;
- means for storing a plurality of leaflets;
- means for storing a plurality of adhesively activatable tab members;
- leaflet applicator means disposed at said leaflet application station for receiving a tab member and a leaflet such that the leaflet is superimposed over the center portion of said tab member to form a leaflet/tab combination, and applying a tab/leaflet combination to a container, said leaflet applicator means including means for adhesively activating only the end portions of each tab member;

label applicator means disposed at said label application station and downstream of said leaflet applicator means for receiving a label from said label storage means and applying said label to a container while the container is in motion as it passes said label application station, said label applicator means including means for adhesively activating said label before it is applied to a container;

control means for mating each leaflet with a tab on said leaflet applicator means, and for mating each tab/leaflet combination with a container; and control means for selectively operating said label applicator means at the precise time one of said spaced apart containers passes said label applicator means.

21. An apparatus as in claim 20 which further includes orientation means, disposed at said entry station, for receiving each of said containers in a vertical position and placing each of said containers in a horizontal position for conveyance through the apparatus.

22. An apparatus as recited in claim 21 wherein said orientation means comprises a curved rail member for receiving said container in a vertical position and rotating said container to a horizontal position.

23. An apparatus as in claim 20 which further includes reorientation means, disposed adjacent said exit station, for receiving each of said containers in a horizontal position and placing each of said containers in the vertical position for discharge from the apparatus exit station.

24. An apparatus as in claim 23 wherein said reorientation means comprises a plurality of spaced apart rotatable gripper members disposed on either side of said conveyor means; means for bringing together an opposed pair of said gripper members for gripping each of said containers; means for rotating said gripper members to effect the rotation of each container from the horizontal position to the vertical position; and means for withdrawing said opposed pair of gripper members to effect the release of each container after it has been reoriented.

25. An apparatus as in claim 20 which further includes label securing means disposed downstream of said label applicator means for wiping the ends of each label against the sides of the container to which said label is applied so as to secure said label to each container.

26. An apparatus as in claim 20 which further comprises first container stabilizing means disposed opposite said leaflet applicator means for exerting a force against each container substantially opposite to that exerted by said leaflet applicator means as each tab/leaflet combination is applied to a container.

27. An apparatus as in claim 20 which further comprises: second container stabilizer means for maintaining the orientation of the containers after label application and while the labels are being secured to the containers by said label securing means, second stabilizer means comprising an endless belt member that engages the top surface of each container and exerts a downward force thereon during the operation of said label securing means.

28. An apparatus as in claim 20 which further comprises:
detector means disposed adjacent said container exit station for detecting the absence of a label or tab/leaflet combination; and means responsive to said detector means for discarding any container which does not have a label or tab/leaflet combination.

29. A high speed apparatus for applying labels to containers in a continuous through put operation, the apparatus having container entry and exit stations and a label applicator station, comprising:

conveyor means for transporting said containers through the apparatus from said entry station to said exit station at a constant predetermined speed and in a predetermined spaced relationship with one another;

means for feeding a continuous label web to said label application station, said label web having label indicia and particularly oriented verification marks disposed therein for each individual label;

means disposed upstream of said label application station for cutting each individual label from the label web;

means for conveying said cut individual labels to said application station;

label applicator means disposed at said label application station for receiving a cut label and applying said label to a container while the container is in motion as it passes said label application station;

control means for selectively operating said label applicator means at the precise time one of said spaced apart containers passes said label applicator means; and label securing means including: an endless belt member disposed downstream of said label application station; a pair of rotatable drive rollers for rotating said endless belt member; a pair of parallel longitudinal linkage bar members each of which being disposed on one side of said container conveyor means and connecting the coplanar lateral faces of said drive rollers; and a longitudinal wiper member suspended from each of said linkage bar members such that as said drive rollers rotate each of said wiper members oscillates along with its associated linkage bar member so as to wipe down and secure each label to the sides of its associated container.

30. A high speed method of applying in succession a folded leaflet and a label to a container in a continuous single run operation comprising the steps of:

transporting the containers in a horizontal position through the apparatus at a predetermined constant speed and in a predetermined spaced apart relationship with one another;

transporting folded leaflets to a leaflet application station at a predetermined constant speed, and in a predetermined spaced apart relationship with one another;

feeding an adhesively activatable tab member toward the leaflet application station;

adhesively activating the end portions of said tab member;

mating said activated tab member with a leaflet such that the leaflet is disposed on the non-adhesive portion of said tab to form a leaflet-tab combination;

applying at said leaflet application station said leaflet-tab combination to one face of said container;

feeding an adhesively activatable label to a label application station disposed downstream of said leaflet application station;

adhesively activating said label; and applying said adhesively activated label to the opposed face of said leaflet bearing container as the container is being transported past the label application station.

31. A method as recited in claim 30 which further comprises the step of stabilizing the orientation of said container during the leaflet application step said stabilizing step comprising the step of exerting a downward force on one face of each container as a tab-leaflet combination is being applied to the other face of the container.

* * * * *

UNITED STATES PATENT AND TRADEMARK OFFICE
CERTIFICATE OF CORRECTION

PATENT NO. : 4,351,679
DATED : September 28, 1982
INVENTOR(S) : Hans C. Dreher

It is certified that error appears in the above-identified patent and that said Letters Patent is hereby corrected as shown below:

Column 5, delete line 50 and substitute therefor:

--plastic label 61 for applicator to a container
6. Referring to Figure 3, control means (not
shown) causes label applica- --

Column 6, line 17, change "a" to --as--

Claim 15, line 3, change "such" to --each--

Signed and Sealed this

First Day of March 1983

[SEAL]

Attest:

GERALD J. MOSSINGHOFF

Attesting Officer — Commissioner of Patents and Trademarks